(12) United States Patent
Marshall

(10) Patent No.: US 6,517,809 B1
(45) Date of Patent: Feb. 11, 2003

(54) PROCESS FOR PREPARING A REACTIVE PHARMACEUTICAL PRODUCT FOR THE DETECTION OF GASTROINTESTINAL DISORDER CAUSED BY BACTERIA IN THE GASTROINTESTINAL SUPERIOR TRACT

(76) Inventor: Barry J. Marshall, 40 Beatrice Street, Dalkeith, Western Australia 6009 (AU)

( * ) Notice: Subject to any disclaimer, the term of this patent is extended or adjusted under 35 U.S.C. 154(b) by 0 days.

(21) Appl. No.: 09/424,494

(22) PCT Filed: May 28, 1998

(86) PCT No.: PCT/AU98/00395

§ 371 (c)(1),
(2), (4) Date: Aug. 1, 2000

(87) PCT Pub. No.: WO98/53808

PCT Pub. Date: Dec. 3, 1998

(30) Foreign Application Priority Data

May 28, 1997 (MX) .............................. 9703918

(51) Int. Cl.$^7$ .............................................. A61K 51/00

(52) U.S. Cl. .................... 424/1.37; 424/1.29; 424/1.25; 424/1.33; 424/1.81

(58) Field of Search ............................... 424/1.29, 1.25, 424/1.33, 1.21, 1.81, 1.37; 435/12

(56) References Cited

U.S. PATENT DOCUMENTS

| | | |
|---|---|---|
| 3,145,086 A | 8/1964 | Free et al. |
| 3,852,413 A | 12/1974 | Cammarata |
| 3,876,502 A | 4/1975 | Monte et al. |
| 4,101,382 A | 7/1978 | Chang |
| 4,153,685 A | 5/1979 | Sefontein |
| 4,548,805 A | 10/1985 | Sack et al. |
| 4,581,221 A | 4/1986 | Kuperus |
| 4,748,113 A | 5/1988 | Marshall |
| 4,830,010 A * | 5/1989 | Marshall ..................... 128/630 |
| 4,851,209 A | 7/1989 | Vasquez et al. |
| 4,923,801 A | 5/1990 | Marshall et al. |
| 4,947,861 A | 8/1990 | Hamilton |
| 5,256,684 A | 10/1993 | Marshall |
| 5,258,178 A | 11/1993 | Cordle et al. |
| 5,260,057 A | 11/1993 | Cordle et al. |
| 5,304,540 A | 4/1994 | Blackburn et al. |
| 5,314,804 A | 5/1994 | Boguslaski et al. |
| 5,420,016 A | 5/1995 | Boguslaski et al. |

(List continued on next page.)

FOREIGN PATENT DOCUMENTS

| | | | | |
|---|---|---|---|---|
| EP | 0018825 | 2/1985 | | |
| GB | 1112251 | 5/1968 | | |
| GB | 1478742 | 6/1977 | | |
| WO | WO 8909407 | 10/1989 | | |
| WO | WO 9511672 | 5/1995 | | |
| WO | WO 96/14091 | * 5/1996 | .......... | A61K/49/00 |
| WO | WO 9740856 | 6/1997 | | |
| WO | WO 9961892 | 12/1999 | | |

OTHER PUBLICATIONS

U.S. patent application Ser. No. 09/977,555, Marshall, et al., filed Oct. 15, 2001, Method for the Detection of Urease and Method for Using Same.

U.S. patent application Ser. No. 09/977,556, Marshall, et al., filed Oct. 15, 2001, System for the Detection of Urease and Method for Using Same.

U.S. patent application Ser. No. 09/977,874, Marshall, et al., filed Oct. 15, 2001, Composition for The Detection of Gastrointestinal Disorders.

Peura D A, et al.: Microdose 14C–ureaa breath test offers diagnosis of Helicobacter pylori in 10 minutes The American Journal of Gastroenterology (vol. 91, No. 2, 1996) pp 233–238.

Database Medline "Online" US National Library of Medicine (NLM), Bethesda, MD, US; Hamlet et al.: "A simple, rapid, and highly reliable capsule–based 14C urea breath test for diagnosis of Helicobacter pylori infection" & Scandinavian Journal of Gastroenterology (Nov. 1995).

Marshall B J et al.: "A Microdose, capsule–based, 14C–urea breath test for H. pylori," Abstract Gastroenterology, US, Elsevier, New York, NY (May 1, 1991).

Marshall, B.J., et al.: "A 20–Minute Breath Test for Helicobacter Pylori," The American Journal of Gastroenterology, (vol. 86, No. 4, 1991) pp 438–445.

*Primary Examiner*—Michael G. Hartley
(74) *Attorney, Agent, or Firm*—Dority & Manning P.A.

(57) ABSTRACT

The invention relates to the diagnosis in a human or lower animal subject of a gastrointestinal disorder of the upper gastrointestinal tract caused by bacteria using a breath test. In one aspect the invention provides a process for the preparation of a reactive pharmaceutical product for the detection of gastrointestinal disorder caused by bacteria in the superior gastrointestinal tract, characterized by the preparation of a dense powdered vehicle or granules of sugar, or granules of Nu-pareil seeds, of a specific diameter between 0.12 to 3.0 mm and soluble in gastric fluids; dispersing in or coating on the vehicle a micro dose of $^{14}$C-urea; and coating or encapsulating the resulting blend with an inert gelatin substance that dissolves rapidly, thereby obtaining a capsule, wherein the density of the vehicle is such that it allows deposition of the isotope contained in the capsule onto the gastrointestinal tract mucosa.

In another aspect the invention provides a pharmaceutical product for breath tests for the detection of gastrointestinal disorder that comprises an isotope of $^{14}$C-urea dispersed in or coated on a dense powdered or granulated vehicle of sugar, Nu-pareil seeds, and the resulting blend being coated with or enclosed in inert gelatin substance that dissolves rapidly in the presence of gastric juice, wherein the vehicle has a density sufficient to allow the capsule contents to be deposited onto the gastrointestinal tract mucosa, and wherein the granules have a diameter of between 0.12 to 3.0 mm.

20 Claims, No Drawings

U.S. PATENT DOCUMENTS

| | | |
|---|---|---|
| 5,439,801 A | 8/1995 | Jackson |
| 5,479,019 A | 12/1995 | Gross |
| 5,542,419 A | 8/1996 | Moulton-Barrett et al. |
| 5,593,851 A | 1/1997 | Jackson |
| 5,601,848 A | 2/1997 | Marshall |
| 5,668,011 A | 9/1997 | Jackson |
| 5,702,911 A | 12/1997 | Whalen |
| 5,719,052 A | 2/1998 | Ito et al. |
| 5,738,110 A | 4/1998 | Beal et al. |
| 5,846,751 A | 12/1998 | Pronovost et al. |
| 5,848,975 A | 12/1998 | Phillips |
| 5,989,840 A | 11/1999 | D'Angelo et al. |
| 6,060,241 A | 5/2000 | Corthesy-Theulaz |
| 6,067,989 A | 5/2000 | Katzman |
| 6,068,985 A | 5/2000 | Cripps et al. |
| 6,113,875 A | 9/2000 | Nystrom et al. |
| 6,156,346 A | 12/2000 | Chen et al. |
| 6,165,736 A | 12/2000 | Fawcett |
| 6,171,811 B1 | 1/2001 | Becerro De Begon Vallejo |
| 6,183,776 B1 * | 2/2001 | Depui et al. ................ 424/468 |
| 6,187,556 B1 | 2/2001 | Lee et al. |
| 6,228,605 B1 | 5/2001 | Marshall |
| 6,294,151 B1 | 9/2001 | Hayakawa et al. |

* cited by examiner

PROCESS FOR PREPARING A REACTIVE PHARMACEUTICAL PRODUCT FOR THE DETECTION OF GASTROINTESTINAL DISORDER CAUSED BY BACTERIA IN THE GASTROINTESTINAL SUPERIOR TRACT

This application is a 371 of PCT/AU98/00395, filed May 28, 1998.

BACKGROUND OF THE INVENTION

Brief Description of the Prior Art

Factors adversely affecting the function of the gastrointestinal system in humans are exceedingly varied in their nature. Such disorders may arise in the upper or lower gastrointestinal tracts or both. There is a broad range of causes of gastrointestinal disorders, including genetic, physiological, environmental and psychogenic factors. Accordingly, the diagnosis and management of these disorders can be exceptionally difficult.

Among the chronic disorders of the upper gastrointestinal tract are those which fall under the general categories of gastritis and peptic ulcer disease. The gastrointestinal tract is generally defined as including the esophagus, the stomach, the duodenum, the jejunum and ileum. Peptic ulcers are lesions of the gastrointestinal tract lining, characterized by the loss of tissue due to the action of digestive acids and pepsin. It has generally been held that peptic ulcers are caused by gastric hypersecretion, decreased resistance of the gastric lining to digestive acids and pepsin or both. Gastritis is, by definition, an inflammation of the stomach mucosa. In practice, though, the disorder is manifested by a broad range of poorly defined, and heretofore inadequately treated, symptoms such as indigestion, "heart burn", dyspepsia and excessive eructation.

However, the diagnostic methods typically employed in the art are often slow, cumbersome, costly and may yield equivocal or inaccurate results. Such patients may simply be treated with conventional therapies, such as with antacids or drugs which inhibit stomach acid secretion. While such therapies might provide temporal symptomatic relief, a cure is often not effected. In particular, it has been discovered that many such gastrointestinal disorders are mediated by infection of the gastric mucosa by bacteria. Thus treatment of the bacterial infection may be required in order to effectively treat the manifested gastrointestinal disorder.

Accordingly, a simple diagnostic test for gastrointestinal disorders could afford substantial advantages in the proper end effective treatment of patients having gastrointestinal disorders. Such a test should be easily performed, allowing definitive interpretation, and yield a result with a high degree of correlation to the presence or absence of the gastrointestinal disorder.

It was disclosed in U.S. Pat. No. 4,830,010, the subject matter of which is incorporated herein by reference, that gastrointestinal disorders of the upper gastrointestinal tract may be detected and diagnosed by methods involving the administration of urea to a human or lower animal subject followed by analyzing the breath of the subject to detect the presence of products of urea hydrolysis. The methods disclosed in U.S. Pat. No. 4,830,010 provided a rapid, inexpensive, non-invasive diagnosis, however, accuracy was compromised by several factors.

The $^{14}C$-urea was administered in liquid form and caused contamination of the mouth and generation of labelled carbon dioxide from the oropharynx. When the solution of $^{14}C$-urea contacts the oropharynx, a small amount of $^{14}CO_2$ is generated by the hydrolysis of the urea as a result of urease from mouth bacteria contaminating the mouth. This contamination results in the generation of $^{14}CO_2$, which peaks approximately one minute after swallowing the solution and is generally detectable for 12 minutes. In some cases, excessive mouth hydrolysis results in continuation of this peak for up to 20 minutes, producing a possible false positive result. The liquid also was likely to empty quickly from the stomach through the pylorus. This prevented adequate contact between the $^{14}C$-urea and the gastric mucosa, where the bacterial urease of Helicobacter pylori is located. Therefore, urea hydrolysis tended to be slowed and larger doses of isotope or breath volume collection bottles greater than 1.5 liters were necessary. The liquid additionally increased the possibility of spillage and safe transport of the isotope was difficult.

The shelf life of isotope in the solution was short leaving a possibility that contamination of the isotope with microorganisms could result in hydrolysis of the urea. To prevent the contamination, refrigeration and/or the addition of a preservative was necessary.

The breath samples were collected by blowing through a tube into a collecting bottle. Patients exhaled at a different rates, thereby introducing an unwanted variability into the test result. Because of this variability, several samples were necessary and the collection bottles were relative large to prevent spillage of bubbles and solution. It was found that the slow transit of lung air through the mouth caused heavy contamination of breath by labelled $^{14}CO_2$ arising in the oropharynx.

Vászquez and others U.S. Pat. No. 4,851,209 describe in-vivo procedure of in-vivo diagnostics for the clinical evaluation of gastrointestinal ulcer illness that uses radioactive isotopes. The procedure involves the previous administration of a pharmaceutical followed by cintigraphic imagery of the gastrointestinal area of interest, with equipment of cintigraphic imagery.

Even when the use of urease or other indicators have been used in combination with pH indicators, all except Vászquez are conducted in-vitro.

It has now been found that the problems of the prior art relating to the diagnosis in a human or lower animal subject of a gastrointestinal disorder of the upper gastrointestinal tract caused or mediated by bacteria which result in the gastric materials of the subject to contain relatively large quantities of urease, can be overcome through the use of a novel method of detection of urease that uses a reactive encapsulated product for the detection of urease by breath and a device (kit) specially designed for quick tests.

It is therefore an object of this invention to provide a procedure for preparing a reactive product for pharmaceutical use for detecting urease caused by gastrointestinal disorders.

Another object of the present invention is to provide an encapsulated reactive product for pharmaceutical use comprising a safe amount of isotope-labelled urea, that is orally administered, and allows by breath analysis of the subject to determine the presence of the product of the hydrolysis of urea.

DETAILED DESCRIPTION OF THE INVENTION

The present invention relates to with a procedure for obtaining a pharmaceutical product useful to detect a gastrointestinal disorder of the upper gastrointestinal tract in a human or lower animal, as well as the pharmaceutical product thereof.

Accordingly in a first aspect the present invention provides a process for the preparation of a reactive pharmaceutical product for the detection of gastrointestinal disorder caused by bacteria in the superior gastrointestinal tract, characterized by the preparation of a dense powdered vehicle or granules of sugar, or granules of Nu-pareil seeds, of a diameter from 0.12 to 3.0 mm and soluble in gastric fluids; dispersing in or coating on the vehicle a micro dose of $^{14}C$-urea; and coating or encapsulating the resulting blend with a gelatin substance that dissolves rapidly, thereby obtaining a capsule, wherein the density of the vehicle is such that it allows deposition of the isotope contained in the capsule onto the gastrointestinal tract mucosa.

In a second aspect the invention provides a pharmaceutical product for breath tests for the detection of gastrointestinal disorder that comprises an isotope of $^{14}C$-urea dispersed in or coated on a dense powdered or granulated vehicle of sugar, or Nu-pareil seeds, the resulting blend being coated with or enclosed in gelatin substance that dissolves rapidly in the presence of gastric juice, wherein the vehicle has a density sufficient to allow the capsule contents to be deposited onto the gastrointestinal tract mucosa, and wherein the granules have a diameter of from 0.12 and 3.0 mm.

Urea has the formula $H_2NCONH_2$ and is a product that occurs naturally in the metabolism of proteins. The gastric materials of humans or animals that have gastrointestinal disorders, contain relatively large quantities of urease (urea amino hydrolase) if the bacteria *helicobacter pylori* resides in the gastric tissue of the stomach of the subject, this urease hydrolyses the urea to ammonia bicarbonate or ammonia and carbon dioxide. Normally the urease exists in the body in minimum quantities. *H. pylori* increases the amounts of urease above the normal levels leading to an unusually high rate of decomposition of urea in the affected areas. The urease reacts with urea to produce ammonia.

The isotope is encapsulated in a gelatin capsule and delivered to the gastric mucosa along with a dense powdered vehicle of a food product. Sugar, lactose, Nu-pareil seeds (candy beads or sugar spheres), and sucrose granules coated with urea are among the materials which can be used. The term "Nu-pareil seeds" as used herein refers to sugar spheres or candy beads, in particular those comprising a sugar, such as sucrose, and a starch.

The Isotope-labelled Urea is $^{14}C$-urea

The $^{14}C$-urea is added to a dense vehicle dissolvable in gastric juices to approximately 1 to 20 grams per kilogram of vehicle, the preferred vehicles are granules such as Nu-pareils, although other vehicles approved for pharmaceutical use can be used when they have enough density to deposit the capsule in the mucosa of the stomach. The density of the vehicle is critical because it has to be able to migrate to the gastric mucosa. One method of coating the vehicle with the isotope is to spray a solution of the isotope in a volatile solvent, such as alcohol, onto the granules. Preferably the granules are agitated to ensure an even coating. A dye, such as fluorescein, may be added to the solution as an indicator of spills of the isotope solution. A convenient method for agitating the granules is by means of a mixing drum.

The breath sample is collected by exhaling into a non-air permeable bag through an inlet tube. The non-air permeable bag is transported to a testing site and the breath sample is transferred from the non-air permeable bag through use of a low vacuum pump to an analysis solution. The non-air permeable bag can be aluminumized foil or plastic. The non-air permeable bag has an inlet which can be sealed to prevent the breath sample from escaping. An alternate embodiment has a sealable air outlet for removal of the breath sample. A pressure locking strip allows for the bag to be opened and sealed for repeated samples.

In the present invention the natural dispersion of the granules over the mucosa covers an area sufficient to react with at least a few colonies of the bacteria. If granules are used which float, the indicators disperse and do not have a great chance to come into direct contact with the affected area and less rapid or less exact results will ensue.

As mentioned above, other types of dense vehicles approved for pharmacological use can be used in all its line if they are capable of absorbing the required reactives indicators and that they have enough density to ensure the capsule and/or its contents end up resting over the mucosa and dissolve there in a few minutes. When powdered vehicles are used the reactives are combined with the vehicle. This can be dried and if necessary ground to form more powder. The granules have the advantage that they are easy to produce, cover about the same area as a powder with the reactives and give good results.

When $^{14}C$-urea contacts with the oropharynx, a small amount of $^{14}CO_2$ is generated by the hydrolysis of the urea due to the urease from the mouth bacteria contaminating the mouth. The contamination generates $CO_2$ which peaks approximately one minute after swallowing the solution and is detectable for 12 to 20 minutes.

This contamination can produce a "false positive" result to the test. It has been found that when the $^{14}C$-urea solution is administered directly into the esophagus, the oropharyngeal isotope peak does not occur. This is yet another reason why the encapsulated product according to the invention provides a more accurate result as the beads or granules (with their attached indicators) do not come into contact with the oropharynx. Instead, the beads or granules are only exposed to the bacteria when the capsule dissolves in the stomach.

The process for preparing the pharmaceutical vehicle for the detection of gastrointestinal disorder, is characterized by the steps of incorporating a micro curie of isotope of the $^{14}C$-urea in an inert gelatin capsule with a dense soluble granulated or powdered vehicle, where the preferred capsule is manufactured from an inert, gelatin substance, which preferably breaks open after about 1 to 5 minutes. The dense carrier or vehicle, is advantageously a food product such as a sugar, or Nu-pareil seeds in which $^{14}C$-urea is preferably dispersed, to form a dense vehicle, that dissolves rapidly in gastric juice in approximately 1 to 20 grams per L. Additionally, compressed lactose powder or sucrose granule coated with urea can be included.

The pharmaceutical product obtained for the breath tests comprises a micro curie of isotope of the $^{14}C$-urea dispersed in a vehicle of dense powder such as a sugar, or Nu-pareil seeds, or compressed lactose powder or sucrose granules, coated with an inert, gelatin substance, that dissolves rapidly in the gastric juice, with an exact density that allows the capsule to be deposited on the mucosa of the gastrointestinal tract, and with a bead size filtered between a critical diameter of 0.012 to 3.0 mmn, that allows a better placement of dispersion of the $^{14}C$-urea onto the stomach mucosa.

Compressed lactose has suitable solubility and forms a dense solution which utilizes gravity to place the $^{14}C$-urea onto the gastric mucosa. The density of the vehicle draws the $^{14}C$-urea to the bottom of the gastric juice pool, thereby preventing dilution of the $^{14}$C-urea throughout the gastric contents and permitting intimate contact between the isotope and the gastric mucosa.

This is in contrast to the use of a liquid which is liable to empty quickly from the stomach through the pylorus, preventing adequate contact between the urea and the gastric mucosa. Additionally, a liquid vehicle has isotope dispersed throughout its volume rather than specifically adjacent to the gastric lining. Since urease is inactivated in acid, urea within the volume of the gastric juice is unlikely to react, thus leading to a muted or dampened liberation of labelled $CO_2$.

To further ensure that the capsule dissolves, a small volume of water, approximately 20 ml, can be swallowed after the capsule to avoid the possibility that the capsule can lodge in the oesophagus and dissolve there.

The $^{14}$C-urea decomposes more rapidly in the presence of hydrogen ion and even in a solution of pH neutral water. Thus, storage of the urea in the dry medium of the vehicle maintains the $^{14}$C-urea in a stable form.

The capsule decreases the time required for the test to be performed as the radioisotope is quickly broken down in the mucosa, thus declaring the presence of the *Helicobacter pylori*. A large bolus of urea is quickly delivered adjacent to the mucosa and the bacteria as soon as the capsule dissolves and delivers its contents of dense granules (or vehicle). This allows the $^{14}CO_2$ to appear in the breath very rapidly, shortening the breath test time to less than 20 minutes, normally between 10 to 15 minutes. A similar test with liquid solution takes at least 20 minutes for an initial diagnostic sample, and normally at least double the time needed according to the method of the present invention. The shortened time is also because of the elimination of the spurious urease activity and the accompanying variability discussed supra.

In the case where the *Helicobacter Pylori* is not found in the gastric tissue of the subject, the $^{14}$C-urea is not hydrolysed and the $^{14}$C-urea is excreted in the urine of the subject.

The invention will now be described with reference to an example which illustrates a preferred aspect of the present invention. However it is to be understood that the following description of the invention is not to supersede the generality of the invention previously described.

EXAMPLE 1

Capsules according to the invention were manufactured to the following specifications:

37 kBq (1 $\mu$Ci) $^{14}$C-urea (±20%)
0.2 g sugar spheres, NF (±20%)
7.05×10$^{-5}$ g fluorescein sodium 10% (±20%)
1 size 3 gelatin capsule weighing 0.0452 g (±20%)
1 container (clear blister, single dose unit)
1 closure (paper backed foil liner)

The sugar spheres were coated with a solution of $^{14}$C-urea and fluorescein sodium in ethanol by spraying the solution onto the sugar spheres while they are being agitated in a rotating mixing drum. The ethanol evaporates leaving the $^{14}$C-urea coated on the sugar spheres. After coating the granules are encapsulated in the size 3 gelatin capsules using standard apparatus.

The fluorescein sodium is added to the $^{14}$C-urea in ethanol stock solution. This material acts as a yellow dye, allowing for spills to be easily identified. Since $^{14}$C-urea is a weak beta-emitter, it is not easy to detect with traditional survey instrumentation. The fluorescent yellow dye was added as a means of easily detecting the $^{14}$C-urea. The amount added (7.05×10$^{-5}$ g) is inconsequential and is not expected to provide any therapeutic value, especially when compared to the doses normally given to patients for diagnostic use (5 g fluorescein sodium 10% solution for injection). The choice of the 37 kBq (1 $\mu$Ci) administration is in accordance with ALARA (as low as is reasonably achievable) policies of reducing the dose tenfold from early works which utilized 10 $\mu$Ci and 5 $\mu$Ci (370 kBq and 185 kBq respectively). The blister pack provides a secure single-unit package to maintain capsule integrity. In addition, the clear homopolymer film allows for easy capsule inspection.

From preliminary studies utilising these capsules the benefits of encapsulating the $^{14}$C-urea granules were evident. Primarily, the isotope would not come into contact with the oropharynx so there would not be an early $^{14}CO_2$ excretion peak in HP-negative persons. The second benefit was that patients and staff would not be required to handle radioactive liquids which, although not dangerous, were a nuisance to clean up if spilled and could easily leak during shipping. Thirdly, by supplying $^{14}$C-urea to the gastric mucosa in a solid vehicle, it reached the gastric mucosa in a very concentrated form. This proved to be a major advantage because the urea was quickly hydrolyzed causing a large pulse of $^{14}CO_2$ in the breath between 5 and 20 minutes. Because this rapid peak was relatively high, the isotope dose could be reduced relative to prior art methods to 1 $\mu$Ci (37 kBq).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

What is claimed is:

1. A process for the preparation of a reactive pharmaceutical product for the detection of a gastrointestinal disorder caused by the bacteria *Helicobacter Pylori* in the superior gastrointestinal tract, the process comprising the steps of:
   providing a vehicle comprising a powder or granules, the vehicle containing a sugar, the vehicle having a diameter of from about 0.12 mm to about 3.0 mm, the vehicle being soluble in gastric fluids and having a density sufficient for the vehicle to migrate to a gastric mucosa when ingested;
   coating the vehicle with an isotope-labeled urea; and
   encapsulating the coated vehicle with a substance comprising a gelatin.

2. A process as defined in claim 1, wherein the sugar comprises lactose.

3. A process as defined in claim 1, wherein the sugar comprises sucrose.

4. A process as defined in claim 1, wherein the vehicle comprises a mixture of a sugar and a starch.

5. A process as defined in claim 1, wherein the isotope-labeled labeled urea comprises $^{14}$C.

6. A process as defined in claim 1, wherein the vehicle comprises granules, the granules being coated by the urea.

7. A process as defined in claim 1, wherein the vehicle comprises compressed powder.

8. A process as defined in claim 1, wherein the urea is coated on the vehicle in an amount from about 1 gram per kilogram of vehicle to about 20 grams per kilogram of vehicle.

9. A process as defined in claim 1, wherein the substance encapsulating the coated vehicle releases the coated vehicle in an amount of time of from about 1 minute to about 5 minutes after contacting gastric juice.

10. A process for detecting the presence of the bacteria *Helicobacter Pylori* in the superior gastrointestinal tract comprising the steps of:

placing a pharmaceutical product in the gastrointestinal tract of a patient, the product comprising a vehicle that is soluble in gastric fluids and that has a density and size sufficient for the vehicle to migrate to a gastric mucosa when ingested, the vehicle being coated with an isotope-labeled urea, the coated vehicle being encapsulated with a substance comprising a gelatin;

collecting the breath of the patient; and analyzing the breath for the presence of the isotope of carbon, which indicates the presence of urease.

11. A process as defined in claim 10, wherein the isotope-labeled urea comprises $^{14}C$.

12. A process as defined in claim 10, wherein the vehicle comprises a compressed powder.

13. A process as defined in claim 10, wherein the vehicle comprises granules.

14. A process as defined in claim 10, wherein the vehicle comprises a sugar.

15. A process as defined in claim 14, wherein the sugar comprises sucrose.

16. A process as defined in claim 14, wherein the sugar comprises lactose.

17. A process as defined in claim 10, wherein the vehicle comprises a mixture of a sugar and a starch.

18. A process as defined in claim 10, wherein the vehicle has a diameter of from about 0.12 mm to about 3.0 mm.

19. A process as defined in claim 10, wherein the coated vehicle is encapsulated by a gelatin.

20. A process as defined in claim 10, wherein the vehicle is coated with the urea in an amount from about 1 gram per kilogram of vehicle to about 20 grams per kilogram of vehicle.

* * * * *